United States Patent [19]

Halloran et al.

[11] Patent Number: 5,326,483
[45] Date of Patent: Jul. 5, 1994

[54] METHOD OF MAKING CLEAR SHAMPOO PRODUCTS

[75] Inventors: Daniel J. Halloran; Judith M. Vincent, both of Midland, Mich.

[73] Assignee: Dow Corning Corporation, Midland, Mich.

[21] Appl. No.: 19,938

[22] Filed: Feb. 19, 1993

[51] Int. Cl.$^5$ ............ C11D 1/39; C11D 1/835; C11D 3/02

[52] U.S. Cl. ............ 252/174.15; 252/DIG. 13; 252/DIG. 14; 252/174; 424/70; 424/71

[58] Field of Search ............ 252/174.15, DIG. 13, 252/DIG. 14, 174; 424/70, 71

[56] References Cited

U.S. PATENT DOCUMENTS

| | | | |
|---|---|---|---|
| 4,059,227 | 12/1985 | Chandra et al. | 724/70 |
| 4,620,878 | 11/1986 | Gee | 106/287.15 |
| 4,710,314 | 12/1987 | Madrange | 252/117 |
| 4,933,176 | 6/1990 | Van Reeth | 424/70 |
| 5,145,607 | 9/1992 | Rich | 252/547 |
| 5,211,883 | 5/1993 | Yamashina et al. | 252/546 |

FOREIGN PATENT DOCUMENTS 0152194 8/1985 European Pat. Off.
2058103 2/1981 United Kingdom.

OTHER PUBLICATIONS

"Encyclopedia of Shampoo Ingredients", Anthony L. L. Hunting, Micelle Press, 1983, pp. 40 & 143.
"A Silicone Selection Guide for Developing Conditioning Shampoos", Daniel J. Halloran, Soap/Cosmetics/Chemical Specialties, Mar. 1992, pp. 22, & 24–26.

Primary Examiner—Linda Skaling
Assistant Examiner—Kery A. Fries
Attorney, Agent, or Firm—Jim L. DeCesare

[57] ABSTRACT

A clear shampoo is described which contains a cationic oil-in-water emulsion of an amine functional polydimethyl silicone, and a method of making clear and stable shampoo compositions, in which an emulsion of an amine functional siloxane can be added to a shampoo composition without causing cloudiness, and without contributing instability to the shampoo composition whereby phase separation occurs. In accordance with the method, an emulsion of an amine functional siloxane is added to a shampoo composition without the necessity of requiring that a pearling agent be employed for the purpose of disguising cloudiness.

7 Claims, No Drawings

METHOD OF MAKING CLEAR SHAMPOO PRODUCTS

BACKGROUND OF THE INVENTION

This invention is directed to a clear shampoo, and clear shampoo products which contain a cationic oil-in-water emulsion of an amine functional polydimethyl silicone.

In the "Encyclopedia of Shampoo Ingredients" by Anthony L. L. Hunting, Micelle Press Inc. Cranford, N.J. 1983, on Pages 40 and 143, there is described a shampoo formulation Number S052 of Avon Products, Inc. New York, N.Y., known as "New Vitality Conditioning Shampoo", which contains a cationic emulsion. The cationic emulsion is said to be a blend of Amodimethicone Tallowtrimonium Chloride, and Nonoxynol-10, which are the adopted names of The Cosmetic, Toiletry, and Fragrance Association of Washington, D.C., (CTFA).

This silicone containing cationic emulsion has been traditionally known in the hair care art to tend towards the formation of precipitates in anionic detergent systems such as shampoo products. While the silicone containing cationic emulsion is an excellent shampoo ingredient from the standpoint of providing conditioning such as improved wet-combing ease, luster and resistance to dry fly-away, shampoo formulators have heretofore marketed products which contain the cationic emulsion in a form which contains a pearling agent in order to mask any turbidity in their product.

Thus, the "New Vitality Conditioning Shampoo" noted above, includes as an ingredient glycol stearate, a known pearling agent.

A need therefore exists in the personal care market for clear shampoos containing cationic silicone emulsions which can be formulated without the necessity of masking by pearling otherwise turbid products or products having high cloud points.

SUMMARY OF THE INVENTION

This invention relates to a method of making clear and stable shampoo compositions in which an emulsion of an amine functional siloxane can be added to a shampoo composition without causing cloudiness, and without contributing instability to the shampoo composition whereby phase separation occurs.

The invention further relates to a method of making clear and stable shampoo compositions in which an emulsion of an amine functional siloxane can be added to a shampoo composition without the necessity of requiring that a pearling agent be employed for the purpose of disguising cloudiness.

These and other features, objects, and advantages, of the herein defined present invention will become more apparent from a consideration of the following detailed description thereof.

DETAILED DESCRIPTION OF THE INVENTION

The conditioning agent used for purposes of the present invention as a shampoo additive, can be best described as an amine substituted siloxane polymer containing reactive silanol ($\equiv$SiOH) functionality that is stabilized in the form of an aqueous emulsion by means of a cationic surfactant and a nonionic surfactant. The siloxane polymer is represented by the formula:

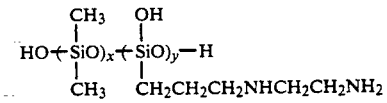

in which x and y are integers having positive values which control the molecular weight of the polymer. Typically, x has a value of from one to about four thousand, and y has a value of from one to about one hundred. When the emulsion is broken, the siloxane polymer is no longer stabilized and may crosslink and cure by condensation of the silanol groups.

An alternate form of the siloxane polymer can be represented by the formula:

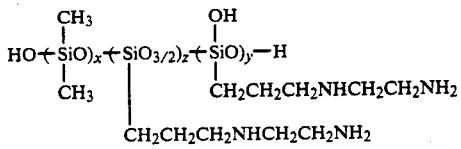

in which x has a value of from one to about four thousand, y has a value of from one to about one hundred, and z has a value of from one to about forty. In his form, the silicone material is a cross-linked film forming polymer which exists in the collodial state.

In either form of the siloxane polymer, the most preferred aminoalkyl group on silicon is the group—$CH_2CH_2CH_2NHCH_2CH_2NH_2$ although other equivalent aminoalkyl groups can be employed as is known in the art. Thus, there may be employed for example radicals such as —$RNHCH_3$; —$RNHCH_2CH_2CH_2CH_3$; —$RN(CH_2CH_3)_2$; —$RNH(CH_2)_6NH_2$; and —$RNHCH_2CH_2CH_2N(CH_3)_2$; in which R is a divalent alkylene radical having from three to six carbon atoms.

The cationic surfactant used to prepare the cationic silicone emulsion is Tallowtrimonium Chloride which is the CTFA adopted name for the quaternary ammonium salt trimethyl tallow ammonium chloride which has the formula $[RN(CH_3)_3]^+Cl^-$ in which R is an alkyl group derived from tallow. The nonionic surfactant used to prepare the cationic silicone emulsion is Nonoxynol-10 which is the CTFA adopted name for an ethoxylated alkyl phenol conforming to the formula $C_9H_{19}C_6H_4(OCH_2CH_2)_nOH$ in which the average value of the integer n is about ten.

This cationic silicone emulsion is available commercially as a product of the Dow Corning Corporation, Midland, Mich. 48686-0994. The silicone content of the emulsion is approximately thirty-five percent by weight.

Such emulsions are oil-in-water type compositions in which the siloxane polymer functions as the internal phase. The particle diameter of he siloxane polymer in the emulsion is typically of the order of magnitude of one hundred nanometers and above, and therefore the emulsions have a milky white appearance to the naked eye, even at high dilutions of 0.1 weight percent for example. It is very surprising therefore that it is possible in accordance with the present invention to formulate clear shampoos from such silicone containing cationic emulsions.

The shampoo composition prepared in accordance with the method of the present invention contains a surfactant such as an anionic, amphoteric, nonionic, or cationic emulsifying agent, and mixtures of such emulsifying agents. The surfactant should provide an acceptable level of foam on the hair and be capable of cleaning the hair.

Suitable anionic surfactants include sulfonated and sulfated alkyl, aralkyl, and alkaryl anionic detergents such as alkyl succinates, alkyl sulfosuccinates, and N-alkyl sarcosinates. Representative detergents are the sodium, magnesium, ammonium, and the mono-, di-, and triethanolamine salts of alkyl and aralkyl sulfates, as well as the salts of alkaryl sulfonates. The alkyl groups of the detergents should have a total of from twelve to about twenty-one carbon atoms, and may be unsaturated. Fatty alkyl groups are preferred. The sulfates may be sulfate ethers containing one to ten ethylene oxide or propylene oxide units per molecule, with two to three ethylene oxide units being sufficient for most purposes.

Typical anionic detergents are sodium lauryl sulfate, sodium lauryl ether sulfate, ammonium lauryl sulfate, triethanolamine lauryl sulfate, sodium C14–16 olefin sulfonate, ammonium C12–15 pareth sulfate, sodium myristyl ether sulfate, ammonium lauryl ether sulfate, disodium monooleamidosulfosuccinate, ammonium lauryl sulfosuccinate, sodium dodecylbenzene sulfonate, triethanolamine dodecylbenzene sulfonate, and sodium N-lauryol sarcosinate.

Particularly suitable anionic surfactants in accordance with the concept of the present invention are compounds such as ammonium lauryl sulfate which is a product sold under the tradename STANDAPOL A, and sodium laureth sulfate which is a product sold under the tradename STANDAPOL ES-3, by Henkel Corp./Emery Grp. Cospha/CD of Ambler, Pa. Sodium lauryl ether sulfate may also be employed, and this product is sold under the tradename EMPICOL ESB 70 by Albright & Wilson Ltd. of Warley, United Kingdom.

Among the various surfactants classified as amphoteric or ampholytic which may be used are cocoamphocarboxyglycinate, cocoamphocarboxypropionate, cocobetaine, N-cocamidopropyldimethylglycine, and N-lauryl-N-carboxymethyl-N-(2-hydroxyethyl)ethylenediamine. Other suitable amphoteric detergents which may be used include betaines and sultaines.

Betaines may have the formula $R'R''R'''N^+(CH_2)_mCOO^-$ in which $R'$ is an alkyl group having twelve to eighteen carbon atoms and mixtures thereof; $R''$ and $R'''$ are lower alkyl groups of one to three carbon atoms and m has a value of one to four. Specific compounds may include alpha-(tetradecyldimethylammonio)acetate, beta-(hexadecyldiethylammonio)propionate, and gamma-(dodecyldimethylammonio)butyrate.

Sultaines may have the formula $R'R''R'''N^+(CH_2)_mSO_3^-$ in which $R'$, $R''$, $R'''$, and m, are the same as defined above. Specific compounds may include 3-(dodecyldimethylammonio)-propane-1-sulfonate, and 3-(tetradecyldimethylammonio)ethane-1-sulfonate.

A suitable amphoteric surfactant for purposes of the present invention is cocamidopropyl betaine which is a product sold under the tradename AMONYL 380BA by Seppic of Paris, France.

Nonionic surfactants suitable for use in the shampoo compositions of the present invention can be fatty acid alkanolamides and amine oxide surfactants. Representative fatty acid alkanolamides include fatty acid diethanolamides such as isostearic acid diethanolamide, lauric acid diethanolamide, capric acid diethanolamide, coconut fatty acid diethanolamide, linoleic acid diethanolamide, myristic acid diethanolamide, oleic acid diethanolamide, and stearic acid diethanolamide. Suitable fatty acid monoethanolamides include coconut fatty acid monoethanolamide. Fatty acid monoisopropanolamides which may be used are oleic acid monoisopropanolamide and lauric acid monoisopropanolamide.

Amine oxide nonionic surfactants suitable for use in the present invention are N-alkyl amine oxides such as N-cocodimethylamine oxide, N-lauryl dimethylamine oxide, N-myristyl dimethylamine oxide, and N-stearyl dimethylamine oxide. Suitable N-acyl amine oxides are N-cocoamidopropyl dimethylamine oxide and N-tallowamidopropyl dimethylamine oxide. N-alkoxyalkyl amine oxides such as bis(2-hydroxyethyl) C12–15 alkoxy-propylamine oxide may also be employed. The hydrophobic portion of the amine oxide surfactant should be provided by a fatty hydrocarbon chain of about ten to twenty-one carbon atoms.

A particularly suitable nonionic surfactant in accordance with the concept of the present invention is cocamide DEA which is a product sold under the tradename MONAMID 1159 by Mona Industries of Paterson, N.J. Linoleic diethanolamide may also be employed and is sold under the tradename EMPILAN 2125 by Albright & Wilson Ltd. of Warley, United Kingdom.

Other nonionic surfactants which may be used are Cocamide MEA sold under the tradename ORAMIDE ML 115 by Seppic of Paris, France, and PEG-120 methylglucose dioleate sold under the tradename GLUCAMATE DOE 120 by Amerchol Corporation, Edison, N.J.

Cationic surfactants useful in the shampoo compositions of the present invention may include those compounds which contain amino or quaternary ammonium hydrophilic moieties in the molecule which are positively charged, such as quaternary ammonium salts. Representative of the various quaternary ammonium salts which may be employed are ditallowdimethyl ammonium chloride, ditallowdimethyl ammonium methyl sulfate, dihexadecyl dimethyl ammonium chloride, di(hydrogenated tallow) dimethyl ammonium chloride, dioctadecyl dimethyl ammonium chloride, dieicosyl dimethyl ammonium chloride, didocosyl dimethyl ammonium chloride, di(hydrogenated tallow) dimethyl ammonium acetate, dihexadecyl dimethyl ammonium acetate, ditallow dipropyl ammonium phosphate, ditallow dimethyl ammonium nitrate, di(coconutalkyl) dimethyl ammonium chloride, and stearyl dimethyl benzyl ammonium chloride. The shampoo compositions of the invention may contain other adjuvants to provide a product which is aesthetically pleasant to the consumer such as thickeners, perfumes, colorants, electrolytes, pH control agents, foam boosters and builders, foam stabilizers, antimicrobials, antioxidants, ultraviolet light absorbers, and medicaments. Such adjuvants however should be carefully selected so as not to cause any turbidity in the final clear shampoo product of the invention.

Thickeners are used to facilitate the hand application of the shampoo composition to the hair, and are added in sufficient quantities to provide a more luxurious effect. Shampoo compositions with viscosities in the range of one thousand to fifteen thousand centistokes measured at twenty-five degrees Centigrade, are generally sufficient. Representative thickening agents which may be used are sodium alignate; gum arabic; guar gum; hydroxypropyl guar gum; cellulose derivatives such as methylcellulose, hydroxypropyl methylcellulose, hydroxyethylcellulose, and hydroxypropylcellulose; starch and starch derivatives such as hydroxyethylamylose and starch amylose; locust bean gum; electrolytes such as sodium chloride and ammonium chloride; saccharides such as fructose and glucose and derivatives of saccharides such as PEG-120 methyl glucose dioleate.

Only cosmetically acceptable perfumes and fragrances should be used to prepare the shampoo composition. Colorants may be added where it is desired to confer a clear hue to the composition. An acid may be employed to adjust the pH within the range of about four to nine. Any water soluble carboxylic acid or mineral acid may be employed. Suitable compounds include mineral acids such as hydrochloric acid, sulfuric acid, and phosphoric acid monocarboxylic acids such as acetic acid, lactic acid, and propionic acid; and polycarboxylic acids such as succinic acid, adipic acid, and citric acid.

Additional conditioners, other than the cationic silicone emulsion, may be added to the shampoo composition in the form of organic cationic conditioning agents for the purpose of providing more hair grooming. Such cationic conditioning agents may include quaternary nitrogen derivatives of cellulose ethers; homopolymers of dimethyldiallyl ammonium chloride; copolymers of acrylamide and dimethyldiallyl ammonium chloride; homopolymers or copolymers derived from acrylic acid or methacrylic acid which contain cationic nitrogen functional groups attached to the polymer by ester or amide linkages; polycondensation products of N,N'-bis-(2,3-epoxypropyl)-piperazine or piperazine-bis-acrylamide and piperazine; and copolymers of vinylpyrolidone and acrylic acid esters with quaternary nitrogen functionality. Specific materials include the various polyquats Polyquaternium-7, Polyquaternium-8, Polyquaternium-10, Polyquaternium-11, and Polyquaternium-23.

Cationic surfactants such as cetyl trimethylammonium chloride, cetyl trimethylammonium bromide, and stearyltrimethylammonium chloride, may also be employed in the compositions as a cationic conditioning agent.

A preservative may be required and representative compounds which may be employed include formaldehyde, DMDM hydantoin, 5-bromo-5-nitro-1,3-dioxane, methyl paraben, propyl paraben, sorbic acid, diazolidinyl urea, and imidazolidinyl urea.

Other adjuvants such as vitamins and therapeutic agents may be added to the shampoo compositions of the present invention provided such adjuvants do not interfere with the clarity of the product.

Clear shampoos prepared in accordance with the teaching of the method of the present invention contain from 3-30 percent by weight of an anionic surfactant as measured on a solids basis; from 0.25-25.0 percent by weight of a cationic silicone emulsion; water in an amount of 50-97 percent by weight; sufficient of an electrolyte to provide a shampoo product having a viscosity of from 1,000-15,000 centistokes and a pH adjusting amount of an acid sufficient to provide a shampoo product with a pH of 4-7.

Clear shampoos are prepared by forming an anionic surfactant solution, adding the cationic silicone emulsion to the anionic surfactant solution, adjusting the pH of the mixture to a value between 4-7, and adding electrolytes and any other desired adjuvants. It is important to add the cationic silicone emulsion to the anionic surfactant solution accompanied by sufficient agitation to provide for a thorough mixing of the ingredients, but not at a speed which would tend to whip the mixture causing the formation of a foam or an aerated mixture. The cationic silicone emulsion should be fed to the anionic surfactant solution at a rate which allows dispersement of the emulsion, and at a temperature at which water is not evaporated. Temperatures less than about thirty-five degrees Centigrade have been found to be most suitable.

While foam boosters and thickeners may be added at any point in the process, they should be added during preparation of the anionic surfactant solution. If additional anionic surfactants are required, such additions should be made following the addition of the electrolytes. Where additional conditioning agents are determined to be required beyond the cationic silicone emulsion, they can be added at any point in the process, although for the best results, it is preferred that they be added as the last ingredient.

The invention is further illustrated in more detail by reference to the following examples and tables.

EXAMPLE I

Five shampoo base formulas were prepared and are shown in Table I. In Table I, "Premix 1" refers an aqueous mixed clear solution containing 350 grams of ammonium lauryl sulfate (30% solids), 30 grams of Cocamide DEA, and 670 grams of water. "Premix 2" refers an aqueous mixed clear solution containing 480 grams of ammonium lauryl sulfate (30% solids), 70 grams of Cocamide DEA, and 450 grams of water. "Emulsion 1" in Table I refers to an amine substituted siloxane polymer containing reactive silanol ($\equiv$SiOH) functionality that was stabilized in the form of an aqueous emulsion by means of a cationic surfactant and a nonionic surfactant. The siloxane polymer had the formula;

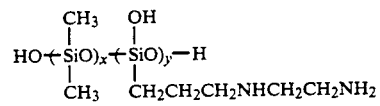

in which x had a value of from one to about four thousand, and y had a value of from one to about one hundred. The cationic surfactant used to prepare the cationic silicone emulsion was Tallowtrimonium Chloride of the formula $[RN(CH_3)_3]^+Cl^-$ in which R was a $C_{16}$ to $C_{18}$ alkyl group derived from tallow. The nonionic surfactant used to prepare the cationic silicone emulsion was Nonoxynol-10 of the formula $C_9H_{19}C_6H_4(OCH_2CH_2)_nOH$ in which n was ten.

"Emulsion 2" was the same as "Emulsion 1" except that the cationic surfactant had an R group of sixteen carbon atoms, and the nonionic surfactant had the formula $C_{13}H_{27}(OCH_2CH_2)_{12}OH$. "Emulsion 3" in Table I was the same as "Emulsion 2" except that the level of cationic surfactant used to prepare "Emulsion 3" was increased four-fold over that of the level of cationic surfactant employed in the preparation of "Emulsion 2".

All of the shampoo base formulas prepared in this example were tested visually with the naked eye and determined to be clear. Shampoo base formulas 3 and 6 were evaluated for their foam production, and wet feel and wet combining on hair tresses. Wet combining was determined using a rating scale of one for the best and five for the worst. Formula 3 performed admirably as a shampoo in these subjective evaluations as shown in Table II, compared to Formula 6 which was a blank containing no silicone emulsion.

tained no cationic silicone emulsion was used as the control. Wet combining was determined using a rating scale of one for the best and five for the worst. Formula 13, which was a shampoo according to the invention, performed admirably in these subjective evaluations following one treatment as shown in Table IV, and following five treatments as shown in Table V.

TABLE III

| Ingredient | Shampoo Base Formulas (Grams) | | | | | | | | |
|---|---|---|---|---|---|---|---|---|---|
| | 8 | 9 | 10 | 11 | 12 | 13 | 14 | 15 | 16 |
| Ammonium lauryl sulfate (30%) | 30 | 48 | 48 | 48 | 48 | 48 | 30 | 240 | 240 |
| Cocamide DEA | 3 | 3 | 8 | 3 | 8 | 3 | 3 | 15 | 35 |
| Hydroxypropyl-cellulose | 1 | — | — | — | — | — | — | — | — |
| Water | 61 | 30 | 40.5 | 43.8 | 33.3 | 45.3 | 64.3 | 226.5 | 225 |
| Emulsion 1 | 2 | 10 | 2 | 2 | 10 | 2 | 2 | 10 | — |
| Citric Acid (pH of shampoo) | 7 | 7 | 7 | 5 | 5 | 5 | 5.1 | 5.7 | 5.8 |
| Ammonium Chloride | 2 | 2 | .5 | 2 | .5 | .5 | .5 | 2.5 | 5 |
| Sodium Chloride | 1 | — | 1 | 1 | 0 | 1 | 0 | .5 | — |
| Sodium lauryl ether (3) sulfate | — | — | — | .2 | .2 | .2 | .2 | 1.0 | — |
| visual | clear | clear | clear | clear | clear | clear | clear | clear | clear |

TABLE I

| | SHAMPOO BASE FORMULAS (Grams) | | | | |
|---|---|---|---|---|---|
| Ingredient | 1 | 2 | 3 | 6 | 7 |
| Premix 1 | 15 | 15 | — | — | — |
| Premix 2 | — | — | 15 | 15 | 15 |
| Emulsion 1 | — | .9 | .9 | — | .9 |
| Emulsion 3 | .9 | — | — | — | — |
| Citric Acid | pH 5.5 | pH 5.5 | pH 5.5 | pH 5.5 | pH 5.0 |
| NH₄Cl | .16 | .16 | .12 | .1 | — |
| Visual | clear | clear | clear | clear | clear |

TABLE II

| | SUBJECTIVE HAIR EVALUATION | | |
|---|---|---|---|
| Shampoo | Foam | Wet Feel | Wet Combing (1 = best, 5 = worst) |
| Formula 3 | excellent | good | 2 |
| Formula 6 | excellent | good | 4 |

EXAMPLE II

Nine additional shampoo base formulas were prepared and are shown in Table III. In Table III, "Emulsion 1" is the same as "Emulsion 1" in Example I and Table II. The shampoo base formulas shown in Table III were prepared by first combining water, ammonium lauryl sulfate, Cocamide DEA, and the cellulose polymer. The cationic silicone "Emulsion 1" was added, and the mixture was stirred at a rate sufficient to disperse the emulsion, but at a rate to avoid whipping of the mixture, foam formation, or aeration of the mixture. The pH of the mixture was adjusted with citric acid to a value as shown in the table. Ammonium chloride was added and mixed, followed by the addition of sodium chloride. Sodium lauryl ether (3) sulfate was added as the last ingredient and accompanied with agitation.

All of the shampoo base formulas prepared in this example were tested visually with the naked eye and determined to be clear. Shampoo base formulas 13 and 16 were evaluated for their wet combining on three types of hair tresses including "Fine Hair", "Bleached Hair", and "Damaged Hair". Formula 16 which con-

TABLE IV

| SUBJECTIVE EVALUATION OF WET COMBING | | | |
|---|---|---|---|
| One Treatment (1 = best, 5 = worst) | | | |
| Shampoo | Fine Hair | Bleached Hair | Damaged Hair |
| Formula 13 | 1.67 | 2.67 | 4.33 |
| Formula 16 | 2.67 | 3.33 | 5 |

TABLE V

| SUBJECTIVE EVALUATION OF WET COMBING | | | |
|---|---|---|---|
| Five Treatments (1 = best, 5 = worst) | | | |
| Shampoo | Fine Hair | Bleached Hair | Damaged Hair |
| Formula 13 | 2 | 3 | 4 |
| Formula 16 | 5 | 5 | 5 |

EXAMPLE III

In order to illustrate the importance of proper mixing of the cationic silicone emulsion into the shampoo base formula, "Shampoo Base Formula 13" in Table III was prepared at five different mixing speeds as shown in Table VI. The "Mixing Setting" corresponds to the position of an air valve used to drive a standard laboratory mixer. A valve setting of 1/16 produces a very slow rate of rotation, whereas a setting of ½ produces an extremely rapid rate of rotation. As can be seen in Table VI, hazy shampoos were produced at all rates except the rate corresponding to the "Mixing setting" of ⅜. The ⅜ setting produced a clear shampoo, and was determined to be the rate at which the cationic silicone emulsion could be added without producing whipping, foaming, or aeration, of the mixture.

TABLE VI

| Mixing Setting | Result (24 Hours) |
|---|---|
| 1/16 | Hazy |
| ⅛ | Hazy |
| ¼ | Hazy |
| ⅜ | Clear |
| ½ | Hazy |

EXAMPLE IV

In order to illustrate the importance of employing the proper processing temperature for preparation of the shampoo, "Shampoo Base Formula 13" in Table III was prepared at four different processing temperatures as shown in Table VII. Table VII reveals that low temperature processing is required to produce clear shampoos including the cationic silicone emulsion. Thus, clear shampoos were produced at temperatures generally in the range of 9-34 degrees Centigrade. Temperatures in the range of five to thirty degrees Centigrade are generally sufficient for purposes of the present invention.

TABLE VII

| Process Temperature (°C.) | Result (24 Hours) |
|---|---|
| 9 | Clear |
| 21 | Essentially Clear |
| 34 | Hazy |
| 51 | Very Hazy |

Prior to the present invention, attempts by those skilled in the art to formulate clear shampoos containing cationic silicone emulsions have been unsuccessful. Yet, clear shampoos provide the consumer with desired benefits, since such products imply a consumer perception of purity, naturalness, and health. Thus, a need clearly exists in the personal care arena for such clear shampoo products.

Prior unsuccessful efforts by those skilled in the art have been based on the belief that the use of cationic silicone emulsions in a shampoo environment which contains a high level of anionic surfactant, causes such systems to rapidly form insoluble precipitates. The formation of such precipitates has been theorized in terms of cationic/anionic surfactant interactions which are considered to be unavoidable. The present invention however provides a viable method for producing such clear shampoo products without the formation of insoluble precipitates which would tend to interfere with product clarity.

Other variations and modifications may be made in the compounds, compositions, and methods, described herein without departing from the essential features and concepts of the present invention. The forms of the invention described herein are exemplary only and are not intended as limitations on the scope of the invention as defined in the appended claims.

That which is claimed is:

1. A method of making a clear shampoo composition containing a silicone cationic emulsion comprising the steps of (i) forming an aqueous solution of an anionic surfactant, the anionic surfactant being present in an amount of from 3 to 30 percent by weight on a solids basis, based on the total weight of the clear shampoo composition; (ii) adding to the aqueous solution at a temperature of from 5 to 30 degrees Centigrade from 0.25 to 25 percent by weight based on the total weight of the clear shampoo composition of a silicone containing cationic emulsion which is an amine substituted siloxane polymer having reactive silanol functionality that is stabilized in the form of an aqueous emulsion by means of a cationic surfactant and a nonionic surfactant, the siloxane polymer being present in the cationic emulsion in the form of particles having a diameter of at least about one hundred nanometers; (iii) mixing the solution containing the cationic emulsion at a rate sufficient to disperse the siloxane polymer, but at a rate less than that which would cause the solution to foam or become aerated; (iv) adjusting the pH of the solution to a value of from 4 to 7; (v) and adding an electrolyte to the solution in an amount sufficient to provide a clear shampoo composition having a viscosity of from 1,000 to 15,000 centistokes; the total water content of the clear shampoo composition being from 50 to 97 percent by weight.

2. A method according to claim 1 in which the electrolyte is a compound selected from the group consisting of sodium chloride and ammonium chloride.

3. A clear shampoo composition prepared in accordance with the method defined in claim 1.

4. A method of shampooing and conditioning hair comprising the steps of applying the clear shampoo composition defined in claim 3 to hair, rubbing the clear shampoo composition into the hair, and removing the composition from the hair by rinsing the hair with water.

5. A method of making a clear shampoo composition containing a silicone cationic emulsion comprising the steps of (i) forming an aqueous solution of an anionic surfactant, the anionic surfactant being present in an amount of from 3 to 30 percent by weight on a solids basis, based on the total weight of the clear shampoo composition) (ii) adding to the aqueous solution at a temperature of from 5 to 30 degrees Centigrade from 0.25 to 25 percent by weight based on the total weight of the clear shampoo composition of a silicone containing cationic emulsion which is an amine substituted siloxane polymer having reactive silanol functionality that is stabilized in the form of an aqueous emulsion by means of a cationic surfactant and a nonionic surfactant; (iii) mixing the solution containing the cationic emulsion at a rate sufficient to disperse the siloxane polymer, but at a rate less than that which would cause the solution to foam or become aerated; and (iv) adjusting the pH of the solution to a value of from 4 to 7.

6. A clear shampoo composition prepared in accordance with the method defined in claim 5.

7. A method of shampooing and conditioning hair comprising the steps of applying the clear shampoo composition defined in claim 6 to hair, rubbing the clear shampoo composition into the hair, and removing the composition from the hair by rinsing the hair with water.

* * * * *